United States Patent [19]

Tomlinson et al.

[11] 4,048,300
[45] Sept. 13, 1977

[54] DENTAL PREPARATION CONTAINING MATERIALS HAVING CALCIUM AND PHOSPHATE COMPONENTS

[75] Inventors: Kenneth Tomlinson, Bramhall; Edward John Duff, Sandbach, both of England

[73] Assignee: Colgate-Palmolive Company, New York, N.Y.

[21] Appl. No.: 653,998

[22] Filed: Jan. 19, 1976

Related U.S. Application Data

[63] Continuation of Ser. No. 431,945, Jan. 9, 1974, abandoned.

[30] Foreign Application Priority Data

Jan. 11, 1973 United Kingdom .............. 1633/73
July 25, 1973 United Kingdom ............ 35459/73
July 25, 1973 United Kingdom ............ 35471/73

[51] Int. Cl.$^2$ ............................................. A61K 7/18
[52] U.S. Cl. ....................................... 424/52; 424/49; 424/57; 424/128; 424/140; 424/145; 424/151
[58] Field of Search ........................... 424/52, 128, 57

[56] References Cited

U.S. PATENT DOCUMENTS 3,175,951  3/1965  Tucker et al. ....................... 424/128
3,679,360  7/1972  Rubin et al. ......................... 424/128

OTHER PUBLICATIONS

Legeros et al., *Chemical Abstracts* 66:91794p, (1967).
Whippo et al., *Chemical Abstracts* 68:24958y, (1968).
Duff, *Chemical Abstracts* 74:46349(b), (1971).
Duff, *Chemical Abstracts* 74:79573y, (1971).
Duff, *Chemical Abstracts* 75:40992e, (1971).
Duff, *Chemical Abstracts* 75:136,675e, (1971).
Duff, *Chemical Abstracts* 76:6679u, (1972).
Duff, *Chemical Abstracts* 76:37950e, (1972).
Duff, *Chemical Abstracts* 77:10396n, (1972).
Duff, *Chemical Abstracts* 77:10398q, (1972).
Ramsey et al., *Chemical Abstracts* 78:132811k, (1973).

*Primary Examiner*—Norman A. Drezin
*Attorney, Agent, or Firm*—Robert L. Stone; Murray M. Grill; Herbert S. Sylvester

[57] ABSTRACT

Dental preparations containing materials having calcium and phosphate components are described. Such materials are typically fluorapatite, fluorohydroxyapatite, hydroxyapatite prepared by alternately changing the pH from about 7 to about 4 to about 7 several times, including such materials which have incorporated therein ions such as monofluorophosphate and carbonate or divalent ions such as zinc or fluoranions of a metal such as zinc, e.g. $ZnF_4^{-2}$.

31 Claims, No Drawings

DENTAL PREPARATION CONTAINING MATERIALS HAVING CALCIUM AND PHOSPHATE COMPONENTS

This is a continuation of application Ser. No. 431,945 filed Jan. 9, 1974 and now abandoned.

BACKGROUND

This invention relates to dental preparations which provide highly desirable and unique effects particularly in the inclusion of materials having calcium and phosphate components or moieties.

Salts of calcium phosphates such as dicalcium orthophosphate dihydrate (DCPD), anhydrous dicalcium orthophosphate (ADCP) and calcium pyrophosphate have long been used in oral preparations such as toothpastes for the polishing and abrasive effects which they provide. Other materials containing calcium and phosphate, such as fluorapatite, have been disclosed for use in order to prevent caries. In particular, the article "Prevention of Dental Caries by Brushing the Teeth with Powders Containing Fluorapatite," McClendon and Foster, *Journal of Dental Reasearch, Vol,* 26, No. 3, July, 1947, pages 233–238, describes the use of an impure fluorapatite, powdered rock phosphate (71.4% fluorapatite), or a synthetic fluorapatite to reduce caries in vivo. The synthetic fluorapatite may be made by solution techniques of dropwise addition of lime water, orthophosphoric acid and sodium fluoride to distilled water or by adding alcohol and glycerine plus menthol or thymol to hydroxyapatite and then adding sodium fluoride thereto. A further article, "Orthophosphates. Part II. The Transformations Brushite→Fluoroapatite and Monetite→Fluoroapatite in Aqueous Potassium Fluoride Solution," Duff, *Journal of the Chemical Society,* Section A, 1971, pages 33–38 describes the chemical transformation of secondary calcium orthophosphates into a potassium-containing fluorapatite.

Hydroxyapatite, which is a material containing calcium and phosphate, has been used to promote remineralisation of tooth enamel as in U.S. Pat. No. 3,679,360, patented July 25, 1972 by Rubin and Childress, assignors to the United States of America, as represented by the Administrator of the National Aeronautics and Space Administration. In that patent, dicalcium orthophosphate dihydrate in a gel containing orthophosphate ions and a calcium salt, such as calcium nitrate, is applied to a damaged tooth and hydroxyapatite crystals are formed over a period of time.

It is an advantage of this invention that dental preparations are provided which contain calcium and phosphate components or moieties which provide desirable effects in the oral cavity such as controlled polishing or abrasivity, prophylactic advantages such as remineralisation, reduction of caries incidence or extent or reduction of bleeding from gums and cosmetic advantages such as increased white appearance of teeth.

It is a further advantage of this invention that novel and unique procedures are provided for preparing the desirable calcium and phosphate materials. Other advantages of the invention will be apparent from consideration of this specification.

SUMMARY OF THE INVENTION

In accordance with certain of its aspects, this invention relates to a dental preparation which comprises a dentally acceptable carrier and from about 10% by weight to about 90% by weight of a material containing calcium and phosphate components which material is selected from the group consisting of:

1. analytically pure fluorapative (FA);
2. FA having the crystal morphology of Brushite;
3. FA having monofluorophosphate ions incorporated in the crystal lattice thereof and having the crystal morphology of Brushite;
4. FA having the crystal morphology of Monetite;
5. FA having monofluorophosphate ions incorporated in the crystal lattice thereof and having the crystal morphology of Monetite;
6. Hydroxyapatite (HA) having monofluorophosphate ions incorporated in the crystal lattice thereof;
7. HA having cabonate ions incorporated in the crystal lattice thereof;
8. HA having a complex fluoro anion of a nontoxic transition metal incorporated in the crystal lattice thereof;
9. Fluorohydroxyapatite (FHA);
10. FA wherein a portion of the calcium ion thereof is replaced by another non-toxic divalent cation;
11. FHA wherein a portion of the calcium ion content thereof is replaced by another nontoxic divalent cation;
12. HA wherein a portion of the calcium ion content thereof is replaced by another nontoxic divalent cation;
13. DCPD wherein a portion of the calcium ion content thereof is replaced by another nontoxic divalent cation;
14. ADCP wherein a portion of the calcium ion content is replaced by another non-toxic divalent cation;
15. Calcium pyrophosphate wherein a portion of the calcium ion content thereof is replaced by another non-toxic divalent cation;
16. Mixtures of any two or more of the foregoing materials;
17. Mixtures of any one or more of said foregoing materials with another dental polishing agent; and
18. Mixtures of any one or more of said foregoing materials which contain fluoride or monofluorophosphate in the crystal lattice thereof with a water-soluble fluoride-providing salt.

ANALYTICALLY PURE FA

An analytically pure FA can be formed by reaction of dicalcium orthophosphate dihydrate (DCPD, DCP.2H$_2$0 or CaHPO$_4$.2H$_2$O), mineralogically known as Brushite, with an aqueous solution of hydrogen fluoride or of ammonium fluoride. The crystal morphology of Brushite is of lamella shaped, plate-like, monoclinic crystals. The term "analytically pure" connotes that cations from any of the components of the reactant system are not introduced into the lattice of the FA reaction product, such as would occur, for instance, if an alkali metal fluoride were employed in the solution reaction. The reaction typically proceeds in the presence of an organic base or ammonia for buffering purposes, particularly if hydrofluoric acid reactant is employed. Triethanolamine is the preferred organic base. The pH at the start of the reaction is desirably between about 5 and about 8, since at lower pH values some calcium fluoride may form and at higher pH values some HA may form. A preferred pH range is from about 5.5 to about 7, most preferably 6.5. Fluoride ion diffuses into the DCPD and induces a solid state transformation reaction which forms the FA and is accompanied by a drop in pH of the supernatant liquor. The reaction proceeds easily at from room temperature for about 7 days to about 100° C for about 2 days. Preferably, the reaction is conducted at about 90° C for at least 2 days. The fluoride reactant is employed in amount of fluoride anion ranging fro stoichiometric to about 1.1 times the stoichiometric amount of DCPD. Greater relative amounts of fluoride promote the formation of calcium fluoride which would be analytically pure if the stoichiometric excess were to be 2.5 times. The preferred amount of fluoride for the formation of analytically pure FA is about 1.05 times the stoichiometric amount.

FA is desirable for its potential ability to remineralise carious lesions and to provide fluoride to protect dental enamel. It can also act as a polishing material.

The solution technique described above provides analytically pure FA without resorting to closed reaction conditions or to high temperature synthesis using high reaction temperatures such as greater than 1000° C, which have been previously used in the art.

FA HAVING BRUSHITE OR MONETITE CRYSTAL MORPHOLOGY

It is a desirable aspect of this invention to provide a FA material which has potential remineralising and enamel-protecting properties and also has the highly desirable polishing or abrasive properties of DCPD or anhydrous dicalcium orthophosphate (ADCP or CaHPO$_4$), mineralogically known as Monetite. This is accomplished by preparing FA from DCPD or ADCP or selected amounts in mixtures of these materials, typically ranging from ratios of DCPD to ADCP of from about 10:1 to about 1:10 preferably about 10:1 to about 1:1.

The reaction is carried out by reacting the calcium orthophosphate salt (DCPD, ADCP or mixtures thereof) with an alkali metal fluoride, such as sodium fluoride or potassium fluoride, and preferably sodium fluoride, in a mole ratio of the calcium orthophosphate salt (not including water or crystallisation) to fluoride anion of from about 5:1 to about 1:1, preferably about 5:1. The reaction proceeds easily to completion in aqueous solution at from room temperature to about 100° C, preferably about 90° C. An organic base such as triethanolamine may be employed to control the pH near neutrality. It is desirable to carry out the reaction in a compatible, inert plastic vessel, such as one made of polyethylene.

The FA reaction product has the crystal morphology of Brushite and/or Monetite, as the case may be.

In the foregoing procedures wherein the Brushite and/or Monetite crystal morphology is retained, a portion of the calcium component of the FA reaction product is replaced by the alkali metal cation of the fluoride salt reactant.

If desired, the proportions of DCPD and alkali metal fluoride can be adjusted, particularly when the reaction temperature is above 40° C, to give controlled ratios of FA and ADCP, both having the crystal morphology of Brushite. Similarly, reaction proportions and temperature (preferably 90° C) using ADCP and alkali metal fluoride can be adjusted to partially form FA and thereby produce a mixture of FA and ADCP, both having the crystal morphology of Monetite.

pH FLUCTUATION TECHNIQUES

In accordance with certain further aspects of this invention, materials containing calcium and phosphate components have been prepared by procedures which render them particularly useful for protecting dental enamel. The calcium and phosphate material suspended in an oral or dental carrier can become lodged in the pits and fissures of the teeth and thereby provide a long term source of components necessary to protect teeth from decay. The material can also provide a source of components necessary for remineralisation of the calcified tissue.

The pH of salivary fluids in the human mouth varies within wide limits, (typically between about 4.5 and about 7.5) and conditions are thereby created which promote the growth and development of crystals of HA, FHA and Fa. Such crystals are chemically identical with those of human tooth enamel and their deposition and subsequent in the vulnerable sites on teeth (e.g. the pits and fissures) can repair the tissue and prevent or delay further carious attack.

The pH conditions which promote growth and development of apatite type crystals has led to a procedure in accordance with aspects of this invention whereby materials containing calcium and phosphate can be prepared in controlled purity by synthesis from solution.

For instance, analytically pure FA may be made from a suspension of an aqueous fluoride solution, the pH of the aqueous supernatant being repeatedly fluctuated within the limits pH 4 and pH 7. More specifically, HA which is typically prepared by neutralising orthophosphoric acid with a slurry of calcium oxide is placed in a container with which it is inert and non-active, such as a polyethylene container. Hydrofluoric acid, buffered at pH 7 with a base such as ammonium hydroxide, triethanolamine or the like, is added in about 5% excess of the equimolar amount. The pH is then slowly reduced to 4 by the additon of nitric acid and equilibrium established. A concentrated solution of the base is then again added to return the pH to 7. The pH is then fluctuated to 4 and back to 7, two or more additional times. A sufficient time should be allowed to elapse at each pH 4 and pH 7 level for chemical equilibrium to be established and growth of crystallites to occur. Thus, a period of about 1 hour to about 8 hours, typically about 1 hour to about 3 hours, is provided between each pH swing. The FA reaction product is filtered, washed, for instance about 2 – 5 times with water and then about 2 – 5 times with acetone, and dried. The product is analytically pure FA and is obtained in stoichiometric amount. It is a desirable dental polishing agent or abrasive and has potential remineralising properties. It also provides fluoride to dental enamel.

The foregoing pH fluctuation technique can be modified to provide other calcium and phosphate materials.

FHA can be similarly prepared employing less than an equimolar amount of hydrofluoric acid for reaction with HA. For use as a dental polishing agent or abrasive, the preferred FHA reaction product has the empirical formula Ca$_{10}$(OH)$_{1.6}$F$_{0.4}$(PO$_4$)$_6$.

If in the preparations of FA or FHA, it is desired to include some alkali metal cation in the crystal lattice, hydrofluoric acid reactant can be replaced by the appropriate alkali metal fluoride, e.g. LiF, NaF, KF, RbF, or CsF. Basic buffer to adjust the initial pH of the supernatant solution to 7 would be used only if necessary when alkali metal fluoride reactant is employed.

The fluctuating pH technique for the preparation of FA and FHA can be modified by reacting calcium fluoride with a source of calcium and orthophosphate ions. Thus, this procedure for the production of fluorine-containing apatites comprises dissolving calcium fluoride in acid containing a source of calcium and orthophosphate ions, and raising the pH to about 7 by the addition of a base.

The acidified mixture preferably has a pH of about 4 or below.

A convenient source of the calcium and orthophosphate ions is a soluble calcium orthophosphate salt. Preferably the calcium orthophosphate is used in considerable excess relative to the calcium fluoride, for example, in a molar ratio of 20:1. The minimum molar ratio for the formation of a fluorapatite is 9:1.

Any suitable calcium orthophosphate may be used; for example, those having the formulae: $CaHPO_4$, $Ca_5OH(PO_4)_2$ and $CaHPO_4.2H_2O$.

Where a calcium orthophosphate is employed, the acid is preferably nitric acid.

Instead of, or in addition to, using a calcium orthophosphate, orthophosphoric acid may be used as the source of some or all of the orthophosphate ions. If orthophosphoric acid is used, an additional source of calcium ions besides the calcium fluoride is required, e.g. calcium carbonate or some other calcium salt.

The base used to raise the pH to about 7 is again preferably a volatile base such as ammonia or ammonium hydroxide or triethanolamine, but non-volatile bases such as alkali metal hydroxides can be used if the substitution of alkali metal cations into the fluorapatite can be tolerated.

Instead of using only a single step, the pH may be caused to fluctuate 2–5 times, e.g. three times, between about 4 and about 7, the solution again being allowed to remain for a period of time, e.g. about one hour, at each of the upper and lower pH levels, terminating with a final pH of about 7.

On completion of the reaction the solid product can be removed from the liquid medium by conventional means, e.g. settling or filtration.

The resulting synthetic fluorine-containing apatite may be used for any purpose for which fluorine-containing apatites may be required, e.g. as an ingredient in oral preparations such as dentifrices.

Calcium fluroide is a convenient starting material for several procedures in accordance with this invention. It is also possible to make this compound by fluctuating the pH. Specifically, HA, FA or FHA, which may be empirically expressed as $Ca_{10}(OH)_{2-x}F_x(PO_4)_6$ where $0 \leq x \geq 2$, reacted with hydrofluoric acid in a base buffer of triethanolamine or ammonium hydroxide at pH 7. The pH is then brought to 4 with nitric acid and raised to 7 with the base several times (e.g. 2 – 5 times), thereby forming calcium fluoride when a stoichiometric amount of hydrofluoric acid is used based on the apatite precursor. When less than a stoichiometric amount of hydrofluoric acid is used, a mixture of calcium fluoride and FA results. Other calcium orthophosphates, for example DCPD and ADCP, may also be used in partial or total replacement of the apatite.

In accordance with aspects of this invention, it is desirable to incorporate various ions into calcium and phosphate materials, such as apatites, using the pH fluctuation technique. For instance, monofluorophosphate ions may be incorporated into apatites and thus be available for incorporation into dental enamel as remineralisation occurs. The apatites may be apatite itself or a calcium deficient apatite which may be defined empirically as $Ca_{10-y}H_y(OH)_{2-y}(PO_4)_6.nH_2O$ where $0 \leq n \geq 10$ and $0 \leq y \geq 2$, as well as HA, FHA, or FA. Procedures earlier described for preparing apatite materials such as by pH fluctuation or by providing precursor morphology may be used to obtain the apatite materials.

The novel dental substances containing monofluorophosphate ions are prepared from the corresponding apatite material by repeatedly (say 2 to 5 times) fluctuating the pH of an aqueous solution of a monofluorophosphate containing a suspension of the apatite material, between a pH of about 4 and a pH of about 7, and separating the resulting solid product from the supernatant liquid. For example, sodium monofluorophosphate is dissolved in an aqueous suspension of apatite and the pH is lowered to about 4 by adding a mineral acid such as nitric acid. After a period of time (e.g. one hour) at this pH, a base is added to raise the pH gradually to about 7. Preferably the base is a volatile base, such as ammonium hydroxide, but other bases such as alkali metal hydroxides may be used. After a period of time (e.g. one hour) the suspension is re-acidified and the cycle is separated several times, e.g. 3 times. The resulting apatite into which monofluorophosphate ions have been incorporated, possibly in partial replacement of orthophosphate, is separated from the supernatant liquid by any suitable means, e.g., by settling or filtration, and is the novel dental substance.

The novel dental substances are useful, inter alia, as dental abrasives.

Mixtures of any two or more of these novel dental substances, or mixtures thereof with other dental abrasives such as FA, anhydrous dicalcium phosphate (ADCP), dicalcium phosphate dihydrate (DCP.2H$_2$O) and insoluble sodium metaphosphate (IMP) may be used.

Carbonate ions have also been incorporated into HA employing the pH fluctuation technique in accordance with an aspect of the invention. The product in which the carbonate ions appear to be incorporated in the crystal lattice of HA is quite different from other apatities having carbonate ions associated threwith, which are previously known. The novel carbonate-substituted HA has physical properties which resemble talc without having the undesirable properties which are sometimes attributed to talc and mitigate against its use in cosmetic and other toilet preparations and in oral preparations.

The novel compound is therefore useful as an ingredient in cosmetic and other toilet preparations in complete or partial replacement for talc. Further, it has been discovered that apatites, when used in oral preparations such as dentifrices, can provide a long-term source of components for the remineralisation of the apatite crystal structure of dental enamel. The novel compound of the present invention may be used for a similar purpose in oral preparations such as dentifrices, if desired, in conjunction with a source of additional orthophosphate ions. They also provide a mild abrasive or polishing action for the teeth.

The novel compound may be prepared in various ways. In a preferred method, pH fluctuation as earlier described is employed. An aqueous suspension of hydroxyapatite is acidified to a pH of about 4 and equilibrium established. The pH is then raised to about 7 by the addition of a neutral or basic material providing carbonate ions, such as an alkali metal carbonate or bicarbonate, e.g. sodium carbonate or sodium bicarbonate, preferably the latter. After equilibrium is reached, the suspension is then reacidified by adding acid, and re-neutralized. The cycle may be repeated several times, say 2–5 times.

Desirable aspects of the invention also include partial displacement of calcium from apatite materials such as HA, FA and FHA, which may be provided by procedures earlier disclosed, by other non-toxic divalent metals including alkaline earth metals such as magnesium, strontium and barium and transition metals such as zinc, copper, cadmium, nickel, cobalt, iron, manganese and chromium using pH fluctuation techniques. These divalent metal ions are introduced in amounts such that non-toxicity is retained. Typically they displace about 0.1 –1 cation % of the calcium. Some of these metal ions can provide desirable effects when introduced into the oral cavity. For instance, zinc is known to control gingival bleeding. Various metals are also normally present in dental enamel and their presence in the apatite materials may facilitate their introduction into enamel by remineralisation. For instance, dental enamel can contain zinc, typically in amount of about 2000 ppm.

Zinc-substituted apatitis such as zincsubstituted HA, FA and FHA can be made by reacting a zinc salt with the appropriate apatite compound under conditions of fluctuating pH similar to the techniques earlier described above as for the preparation of FA and FHA. For example, hydroxyapatite may be placed in a container and an aqueous solution of up to $10^{-2}$ M zinc nitrate added thereto. The pH is caused to fluctuate between about 7 and about 4 several times, e.g. 3 times, equilibrium being achieved between each swing. After filtration and washing with water and with an organic solvent such as an acetone, the resulting solid is dried. The concentration of the zinc in the solution controls the degree of substitution of the zinc in the hydroxyapatite.

A similar technique can be used for preparing zinc-substituted FHA from HA, in which the HA is reacted first with a solution of hydrogen fluoride or a soluble salt of the acid, and then with zinc nirate solution, both under fluctuating pH conditions. Alternatively, after zinc-substituted HA is made, zinc-substituted FHA can be prepared by reaction with hydrogen fluoride or a soluble salt of the acid under fluctuating pH conditions.

Buffering to the higher pH value (about 7) may be achieved by the use of a base such as ammonium hydroxide or triethanolamine.

Similar techniques to those described above may be used for the substitution of other divalent ions instead of zinc.

As already indicated, at least some of the zincsubstituted compounds can afford useful inhibition against bleeding of the gums, while those compounds which have the apatite crystal structure are useful for providing dental prophylaxis, e.g. for the protection of teeth against caries. They also provide a source of components suitable for remineralisation of the teeth.

In a modification of the foregoing reaction, it has been surprisingly found that if HA is treated simultaneously with the non-toxic divalent metal ion other than calcium (such as zinc) and a fluoride ion, at the same time under the fluctuating pH conditions, a different end product than divalent metal ion substituted FHA is obtained.

The mechanism is believed to be that instead of the separate replacements of $M^{2+}$ for $Ca^{2+}$ and
$F^-$ for $OH^-$, the two ions enter the crystal lattice of apatite as a complex fluoroanion such as $MF_4^{2-}$ or $MF_6^{4-}$, or as a mixture of both. Such anions replace the orthophosphate groups in apatite.

In a typical example, a slurry of apatite in water is treated with a solution containing $F^-$ ions and $Zn^{2+}$ ions at concentrations of $10^{-2}$M and $10^{-3}$M respectively. The pH of the supernatant liquid is then fluctuated over the pH range 7 to 4 to 7 several times, typically three or four times, by the appropriate additions of nitric acid, and of ammonia or ammonium hydroxide, allowing, say, one hour between each pH adjustment for the establishment of chemical equilibrium. More orthophosphate is released during this reaction than from a control where no added divalent cation is present, thus indicating that some other anion has been incorporated into the apatite. On completion of the reaction, generally at the higher pH level, the solid product can be removed from the liquid medium by conventional means, e.g. settling or filtration.

The principal evidence which leads to the belief that substitution of a complex fluoroanion may occur under conditions of fluctuating pH is that the hydroxyl stretching band in the infra-red of these substituted hydroxy apatites is not diminished unless excess $F^-$ ions are present over and above that required to produce $MF_4^{2-}$ or $MF_6^{4-}$. Fluoride analysis of the solid showed that expected uptake of fluoride had occurred.

If excess $F^-$ is used over and above that required to produce $MF_4^{2-}$ or $MF_6^{4-}$, the hydroxyl band in the infra-red near $3,600$ cm$^{-1}$ is diminished and split, indicating that direct substitution of $F^-$ for $OH^-$ also occurs.

The fluorine-containing apatites of the present invention may be used for any purpose for which fluorine-containing apatites may be required, e.g. as an ingredient in oral preparations such as dentifrice.

Divalent metal ions other than calcium may also be incorporated into other apatites such as FA and FHA by the described pH fluctuation techniques. Such metal-substituted apatites can then be introduced into dental enamel by remineralisation.

A further aspect of the invention provides a method of dental prophylaxis utilizing pH fluctuation in the oral cavity. In this technique, caries are inhibited by supplying fluoride to the teeth while initiating the pH changes with acid and basic materials. The method comprises first applying to the teeth a source of fluoride ions and a weak acidulated phosphate solution comprising an aqueous solution of orthophosphoric acid having a pH of about 3 to about 4, followed by applying to the teeth an aqueous neutralizing solution containing calcium ions and orthophosphate ions.

The teeth are thereby subjected to a fluctuating pH in the presence of fluoride, orthophosphate and calcium ions which, it has been found, not only serves to prevent loss of calcium and orthophosphate ions from the apatite crystal structure of the dental enamel but may also facilitate the growth and development of the apatite crystals so that some remineralisation of pits and fissures in the tooth enamel may occur. Also, laboratory studies have shown that optimum incorporation of fluoride ions into the apatite crystal structure occurs when the pH is rising from about 4 to about 7.

Many variants of the first stage of the treatment are possible. Thus, a variety of water-soluble fluoride salts may be used as the source of fluoride ions. Sodium fluoride is an example. Such salts may be dissolved in the orthophosphoric acid solution. In the case of sources of fluoride ion which are likely to be hydrolyzed by phosphoric acid, such as the alkali metal (e.g. sodium) monofluorophosphates, the first stage of the treatment may involve dissolving the fluoride ion source in the orthophosphoric acid solution immediately before use, or applying the fluoride source and the orthophosphoric acid solution separately and in quick succession to the teeth.

A preferred solution for the first stage of the treatment comprises a dilute aqueous solution of orthophosphoric acid having dissolved therein up to 2% by weight of sodium fluoride, the solution having a pH of about 4.

Preferably, the second or neutralising solution is the supernatant solution obtained in the preparation of synthetic Brushites ($CaHPO_4.2H_2O$). Synthetic Brishite is made by slowly mixing a water-soluble calcium salt and a water-soluble monohydric phosphate salt in aqueous solution at a pH in the range of 4 to 5, using a slight stoichiometric excess of the phosphate. The solution is preferably saturated with calcium and dihydric phosphate ions, but this is not essential.

According to another related aspect of the invention, there is provided a kit comprising: a first container containing an aqueous solution of orthophosphoric acid having dissolved therein up to 2% by weight of a water-soluble fluoride which is not hydrolyzed by orthophosphoric acid, this solution having a pH of about 3 to about 4; and a second container visually distinguishable from the first container and containing an aqueous solution of a water-soluble calcium salt and a water-soluble monohydric or dihydric orthophosphate salt, this solution having a pH of about 7. The previously described method may be carried out easily by use of this kit.

ADDITIONAL MATERIALS CONTAINING CALCIUM AND PHOSPHATE

In addition to the various calcium and phosphate materials described above, additional aspects of this invention relate to further materials containing calcium and phosphate in which a portion of the calcium is replaced by another divalent metal ion.

The substitution of a non-toxic divalent metal ions such as alkaline earth metal ions (other than calcium) and transition metal ions including, for example, zinc, copper, cadmium, nickel, cobalt, iron manganese and chromium into apatites such as HA, FA and FHA has been previously set forth. Such ions may also be incorporated into DCPD or ADCP in order to provide characteristic effects, such as the control of gingival bleeding in the case of zinc ions. When incorporated into DCPD, the divalent ions also can contribute stability to the material and mitigate its transformation into ADCP upon storage. The divalent metal ion typically displaces about 0.1–5 cation % of calcium, and as such is provided in nontoxic amount into the calcium and phosphate material.

Zinc-substituted DCPD can be prepared by reacting an aqueous slurry containing a mixture of calcium oxide and zinc oxide or a mixture of calcium carbonate and zinc carbonate with orthophosphoric acid.

Alternatively, zinc-substituted DCPD can be made be reacting an aqueous solution of a mixture of calcium and zinc halides, for example calcium chloride and zinc chloride, or an aqueous solution of a mixture of calcium nitrate and zinc nitrate, with an aqueous solution of a mixture of monobasic and dibasic sodium orthophosphates, the pH during reaction being no higher than about 5 and preferably in the range from about 4 to about 5. The temperature of the reaction mixture should not rise above 30° C, and preferably be no higher than 20° C.

Non-toxic divalent metal ions other than zinc may similarly displace calcium in DCPD and ADCP by employing compounds of the appropriate metal instead of the zinc compound.

Further, in accordance with a related aspect of the invention, DCPD produced as described above with a portion of calcium replaced by non-toxic divalent metal ions such as zinc ions, can be calcined to produce calcium pyrophosphate polishing agent or abrasive, also substituted by the same amount of non-toxic divalent metal ions. Calcining takes place under suitable temperature conditions, e.g. at about 500° C.

DENTAL PREPARATIONS

The various previously described materials containing calcium and phosphate provide desirable effects in the oral cavity including polishing or abrading, and in some cases remineralising dental enamel.

They are desirably incorporated into dental preparations such as toothpastes, tooth powders, mouth washes and gels for topical application to the teeth.

Of the various calcium and phosphate materials, FA and FHA of Brushite or Monetite morphology or prepared by pH fluctuation techniques, which are analytically pure or which have incorporated therein various desirable ions, such as monofluorophosphate ions or non-toxic divalent metal ions (other than calcium), have been found to be particularly desirable in dental preparations which additionally contain a salt which ionizes in water or saliva to produce a fluoride ion. The apatite material containing fluorine-containing compounds serves to introduce fluoride to pits and fissures of teeth in order to provide anti-caries protection and remineralisation of these parts of the teeth, while the ionisable fluoride-providing compound provides protection against caries through routine dental prophylaxis.

Typical salts which ionise to produce a fluoride ion include:
alkali metal fluorides such as sodium fluoride, potassium fluoride, ammonium fluoride, and fluorides or other metals, such as stannous fluoride or fluoride salts of organic bases, or components which contain fluorine and which may release a fluoride ion on decomposition, e.g.
alkali metal (e.g. sodium, potassium or ammonium) fluorophosphates and difluorophosphates and soluble monofluorophosphates and difluorophosphates of ammonium and other cations, and insoluble monofluorophosphates and difluorophosphates of cations such as calcium. Also soluble silicofluorides such as alkali metal silicofluorides and other complex fluorides.

These salts are typically employed in amount to provide about 0.01 to about 1% by weight of fluoride ion, preferably about 0.1%. Thus, preferred amounts for sodium fluoride, stannous fluoride and sodium monofluorophosphate are 0.3%, 0.4% and 0.76% by weight, respectively.

Dental preparations such as toothpastes and toothpowders normally contain a polishing or abrasive component. The calcium and phosphate materials described herein may be used as the only polishing or abrasive component or components. In order to secure particular polishing or abrasive effects other conventional polishing or abrasive agents may be used in combination with the calcium and phosphate containing material. These include water-insoluble sodium metaphosphate, potassium metaphosphate, tricalcium phosphate, conventionally prepared dihydrated calcium phosphate, conventionally prepared anhydrous dicalcium phosphate, calcium pyrophosphate, magnesium orthophosphate, trimagnesium phosphate, calcium carbonate, alumina including hydrated alumina, aluminium silicate, zirconium silicate, silica, including crystalline silica, and mixtures thereof. Preferred additional polishing materials include insoluble sodium metaphosphate, anhydrous dicalcium phosphate and calcium carbonate, which typically are finely divided and have an average particle size below 10 microns.

Calcium pyrophosphate is also a highly desirable polishing and abrasive agent in combination with calcium and phosphate materials of the invention such as FA and FHA. ADCP/FA mixtures provide a high degree of abrasivity. If even greater abrasivity is desired, mixtures of calcium pyrophosphate and FA or FHA in a weight ratio typically from about 1:10 to about 10:1 are beneficial. If desired, the mixture may be prepared by partially transforming dicalcium phosphate into FA with a predetermined amount of an alkali metal fluoride such as sodium fluoride, filtering and calcining at above 270° C to yield calcium pyrophosphate from the residual dicalcium phosphate in mixture with the already formed FA.

The total polishing or abrasive material of the dental preparation is generally in amounts ranging from about 20 to about 99 by weight of the dental preparation. Preferably, it is present in amounts ranging from about 20% to about 75% in toothpaste and from about 70% to about 99% in toothpowder.

In the preparation of tooth powders, it is usually sufficient to admix meachnically, for example by milling, the various solid ingredients, in appropriate quantities and particle sizes.

Any suitable surface active or detersive material may be included in the dentifrice compositions. Such materials are desirable to provide additional detersive, foaming and anti-bacterial properties, depending upon the specific type of surface active material, and are selected appropriately for the properties desired in the product. These detergents are water-soluble organic compounds usually, and may be anionic, nonionic or cationic in structure. It is preferred to use the water-soluble non-soao or synthetic organic detergents usually. Suitable detersive materials are known and include, for example, the water-soluble salts of higher fatty acid monoglyceride monosulphate detergent (e.g. sodium coconut fatty acid monoglyceride monosulphate), higher alkyl sulphates (e.g. sodium lauryl sulphate), alkyl olefin sulphonates, alkyl aryl sulphonates (e.g. sodium dodecyl benzene sulphonate), higher fatty acid esters of 1,2-dihydroxy propane sulphonate (e.g. sodium coconut fatty acid ester of 1,2-dihydroxy propane sulphonate), suitable mixtures thereof and the like.

The various surface active materials may be used in any suitable amount, generally from about 0.05 to about 10% by weight, and preferably from about 0.5 to 5% by weight, of the dentrifice composition.

Other surface active materials which may be used are the substantially saturated higher aliphatic acyl amides of lower aliphatic amine carboxylic acid compounds, such as those having 12 to 16 carbons in the acyl radical. The amine acid portion is derived generally from the lower aliphatic saturated monoaminocarboxylic acids having about 2 to about 6 carbons, usually the monocarboxylic acid compounds. Suitable compounds are the fatty acid amides of glycine, sarcosine, alanine, 3-aminopropanoic acid and valine having about 12 to about 16 carbons in the acyl group. It is preferred to use the N-lauroyl, myristoyl and palmitoyl sarcoside compounds however for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein reference to "amino carboxylic acid compound", "sarcoside", and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient substantially to affect it adversely, and preferably less than about 10% of said amide material.

In dental cream formulations, the liquids and solids should be proportioned to form an extrudable creamy mass of desirable consistency. In general, liquids in the dental cream will comprise chiefly water, glycerine, sorbitol solution, propylene glycol or polyethylene glycol, such as polyethylene glycol 400, or the like, including suitable mixtures thereof. It is advantageous usually to use a mixture of both water and a humectant or binder such as glycerine or sorbitol. It is preferred to use glycerine. The total liquid content will generally be about 20 – 75% by weight of the formulation. It is preferred to use also a gelling agent in dental creams such as the natural and synthetic gums and gum-like materials, e.g., Irish moss, gum tragacanth, alkali metal, such as sodium, carboxymethylcellulose, hydroxyethyl cellulose, polyvinyl pyrrolidone, starch or water-soluble hydrophilic colloidal polymers and synthetic inorganic silicated clays, such as those sold under the trade marks "Laponite CP" and "Laponite SP," which have the formula

$$[Si_{0.8}Mg_{5.1}Li_{0.6}H_{7.6}O_{28}]^{0.6-} Na^{0.6-},$$

and the like. Certain forms of silica can also be used, such as colloidal silica and silica aerogel. The Irish moss and sodium carboxymethylcellulose are particularly compatible and are preferred gelling agents. The gum content is usually in an amount up to about 10% by weight, and preferably about 0.5 – 5%, of the formulation.

In a gel for topical application to the teeth the calcium and phosphate materials are suspended in a gel medium, which is preferably transparent. The gel medium may comprise a liquid portion and a solid portion which may include the component as described for the dental cream. It is preferred that the liquid portion be about 40 to about 90% by weight of the topical gel and typically includes 0 to about 30% by weight water, 0 to about 80% by weight glycerine and 0 to about 80% by weight of sorbitol solution. Most preferably water, glycerine and/or sorbitol solution are present. The solid portion of the dental medium (i.e. apart from the calcium and phosphate material) is, as in a dental cream, typically present in an amount up to about 10% by weight preferably about 0.5 to about 5% of the formulation.

In the case of a mouthwash, the calcium phosphate material may be suspended in a liquid medium comprising water, preferably aqueous ethyl alcohol. Preferably the ratio of water to alcohol is in the range 1:1 to 20:1, more preferably 3:1 to 20:1 and most preferably about 17:3, by weight. The total amount of water, or aqueous alcohol, in the mouthwash is typically 80 to 95% by weight.

Settlement of the solid phase on standing is not detrimental provided the solid phase can be redispersed on light shaking immediately before use. A suspending agent, which typically is surface active, can be employed if desired. This should be selected having regard to non-toxicity and palatability, and should not have the effect of raising the viscosity of the mouthwash unduly.

Various other materials may be incorporated in the preparations of this invention. Examples thereof are colouring or whitening agents, preservatives, silicones, chlorophyll compounds and ammoniated materials such as urea, diammoniumphosphate and mixtures thereof. These adjuvants are incorporated in the compositions in amounts which do not substantially adversely affect the properties and characteristics, and such amounts are suitably selected depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl) biguanide;
p-chlorophenyl biguanide;
4-chlorobenzyhdryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyl-dimethylammonium) octane dichloride;
5,6-dichloro-2-guanidinobenzimidazole;
$N^1$-p-chlorphenyl-$N^5$-laurylbiguanide;
5-amino-1,3-bis(2-ethoxy)-5-methylhexahydropyrimidine;
and their non-toxic acid addition salts.

Any suiable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitable flavour and sweeting agents may together constitute from about 0.01 to 5% or more of the composition.

The dental preparations should have a pH practicable for use. It is preferred that the initial pH, as determined directly on the preparation, or in the case of a toothpowder on a slurry of the toothpowder in water, be close to neutral and is preferably about 7. Approprite materials may be added to adjust the initial pH if desired.

The following specific Examples are further illustrative of the nature of the present invention, but it is to be understood that the invention is not limited thereto. The compositions are prepared in the usual manner and all amounts of the various ingredients are by weight unless otherwise specified.

EXAMPLE 1

40 grams of DCPD is reacted in a polyethylene container at 90° C with 500 ml of a $10^{-1}$M aqueous solution of hydrogen fluoride in a reaction medium buffered at a pH of 6.5 with triethanolamine. The reaction is permitted to continue for 7 days. The solid product formed is filtered, washed three times with water and is then washed twice with acetone and dried at 100° C.

The product upon examination by chemical analysis, X-Ray diffraction, infra-red spectroscopy and optical microscopy is indicated to be analytically pure FA, $Ca_5F(PO_4)_3$, having a Ca:P ratio of 1.65 - 1.68 and a fluoride content of 3.76 - 3.78%. There is no weight loss upon ignition to 1000° C, indicating no calcium pyrophosphate formation, thereby showing complete conersion of DCPD.

The pure FA reaction product is found upon examination to have the lamella morphology of plate-like monoclinic crystals of the Brushite precursor.

EXAMPLE 2

40 grams of DCPD is reacted in 500 ml of a $10^{-1}$M aqueous solution of sodium fluoride in a polyethylene container at 90° C, the mole ratio of dicalcium phosphate to fluoride ion being 5:1, for a period of seven days to each equilibrium. The solid FA obtained is filtered, washed 3 times with water and then twice with acetone and finally dried at about 60° C.

The FA reaction product, which contains some sodium ions substituted into the crystal lattice of the apatite, upon examination is found to have a lamella morphology of plate-like monoclinic crystals of the Brushite precursor.

In the above reaction, by raising the mole ratio of dicalcium phosphate to fluoride ion to 7:1, a mixture of ADCP and FA, both having the lamella crystal morphology of the Brushite precursor is obtained.

The mixture of FA and ADCP, thus obtained, when subjected to calcining at above 300° C yields a mixture of FA and calcium pyrophosphate, the latter being formed by thermal decomposition of the residual ADCP.

EXAMPLE 3

32 grams of ADCP is reacted in 500 ml of a $10^{-1}$M aqueous solution of sodium fluoride in a polyethylene container at 90° C, the mole ratio of dicalcium phosphate to fluoride ion being 5:1, for a period of seven days to reach equilibrium. The solid FA obtained is filtered, washed and dried as described in previous Examples.

The FA reaction product upon examination is found to retain the crystal morphology of the Monetite precursor.

By raising the mole ratio of ADCP to fluoride ion to 7:1 a mixture of ADCP and FA, both having the crystal morphology of the Monetite precursor is obtained.

The mixture of FA and ADCP thus obtained, when subjected to calcining at above 300° C yields a mixture of FA and calcium pyrophosphate, the latter being formed by thermal decomposition of residual ADCP.

EXAMPLE 4

Orthophosphoric acid is neutralized with an aqueous slurry of calcium oxide to form HA, $Ca_5OH(PO_4)_3$, which is placed in a polyethylene container. An equimolar amount of hydrogen fluoride, in aqueous solution, is added at room temperature as the pH of the reaction medium is maintained at neutrality (7) with 0.880 ammonium hydroxide. The reaction is permitted to reach equilibrium over a period of about two hours.

The pH of reaction medium then reduced to 4 by the slow addition of aqueous 10M nitric acid and equilibrium is again established, over a period of at least one hour.

Ammonium hydroxide is added slowly to restore the pH to 7, at which pH equilibrium is established over a period of at least one hour. Nitric acid is then added slowly to bring the pH to 4, at which pH equilibriun is established over a period of at least one hour.

The pH is repeatedly fluctuated to 7 and back to 4 through an appropriate number of cycles, the final pH being 7, which pH is maintained for at least two hours. The reason for maintaining the pH at the 4 and 7 levels for substantial periods of time is to allow chemical equilibrium to be established and growth of the crystallites to occur. The number of cycles performed depends on the desired efficiency of fluoride incorporation. The greater the number of cycles, the greater the amount of fluoride incorporated. Three cycles may give about 86 – 89% fluoride incorporation whereas 5 cycles may give 95 – 96%. The efficiency of fluoride incorporation may also be improved by increasing the mole ratio of hydrogen fluoride used, up to about 5% excess over that theoretically required to form FA. The FA reaction product is filtered, washed and dried as described in previous Examples.

The FA obtained is stoichiometric (typically the Ca:P ratio is 1.66 – 1.68:1) and is analytically pure as defined above. A typical empirical characterisation of the product is $Ca_5F_{0.95}(OH)_{0.05}(PO_4)_3$.

EXAMPLE 5

Example 4 is repeated except that the reaction ratio between HA and hydrogen fluoride is varied to provide a 70% excess of HA. The reaction product obtained after the repeated pH fluctuation is analytically pure FHA, which can be characterized empirically as $Ca_5(OH)_{0.75}F_{0.25}(PO_4)_3$.

EXAMPLE 6

Calcium fluoride is reacted with DCPD in a mole ratio of 1:9 by dissolving both compounds in a minimum amount of aqueous nitric acid and raising the pH to 7 with 0.880 ammonium hydroxide. Equilibrium is established over a period of two hours. A cyclic fluctuation of pH is repeated as described in Example 4, terminating with equilibrium being established at pH 7. FA is then separated from the reaction medium.

This procedure can be used to produce FHA by decreasing the mole ratio of calcium fluoride to DCPD; for example a 1:18 ratio with produce FHA of the empirical formula $Ca_5F_{0.5}(OH)_{0.5}(PO_4)_3$.

EXAMPLE 7

Example 4 is repeated except that sodium monofluorophosphate is reacted with HA in lieu of hydrogen fluoride. Equilibrium is established a pH 7 and at pH 4 with repeated fluctuations as described, terminating at pH 7. The reaction product contains monofluorophosphate ions in the apatite molecule.

FA and FHA, obtained as in Example 4 and 5 may be used in lieu of HA in order to obtain FA and FHA, each with monofluorophosphate ions substituted therein.

EXAMPLE 7

10 grams of HA are suspended in water and the pH is reduced to about 4 with nitric acid. The suspension is allowed to remain at this pH for about one hour. Sufficient sodium bicarbonate is then added slowly in small amounts to bring the pH to 7. Again, the solution is allowed to remain at this pH value for about one hour. The fluctuation of the pH is repeated as described above, terminating at pH 7. The insoluble product is then recovered from the liquid medium by filtration.

The product has carbonate or substituted in and contained within the apatite structure and has a bulk density less than that of the HA. The surface properties of the product are similar to those of talc.

EXAMPLE 9

50 grams of HA are placed in a polyethylene container and 1 liter of an aqueous solution of $10^{-2}M$ zinc nitrate are added thereto. The pH is adjusted to 7 with 0.880 ammonium hydroxide and allowed to reach equilibrium over a period of 2 Sufficient 10M nitric acid is then added slowly to lower the pH to 4, which is maintained for a period of about one hour. The pH is cyclically fluctuated as described in previous Examples, terminating at pH 7. The reaction product is filtered, washed and dried as previously described.

The product is a hydroxyapatite in which a portion of the calcium is replaced by zinc. It can be represented by the empirical formula $Ca_{4.75}Zn_{0.25}(OH)(PO_4)_3$.

The hydroxyapatite reaction product of this Example can then be adjusted to the reaction procedures of Examples 4 and 5 in place of the HA employed therein to yield FA and FHA products, respectively, in which 5 cation % of the calcium in each is replaced by zinc.

Alternatively, the FA and FHA reaction products of Examples 4 and 5, respectively can be used in the procedure of this Example in place of HA, to obtain FA and FHA products in which 5 cation % of the calcium is replaced by zinc.

EXAMPLE 10

The procedure of Example 9 is modified to include simultaneously $10^{-2}M$ of sodium fluoride with $10^{-3}M$ zinc nitrate in the aqueous solution added to the HA.

In the apatite reaction product, $PO_4^{-3}$ ions are replaced by $ZnF_4^{-2}$ ions.

EXAMPLE 11

The procedure of Example 9 is modified by using cupric nitrate in place of zinc nitrate. The product is a blue coloured hydroxyapatite in which a portion of the calcium is replaced by copper.

Similar blue apatite products are formed when starting with FA and FHA, and also when chromous chloride is used in place of cupric nitrate.

If under 5 cation % of calcium is replaced by copper the bulk density of the product is depressed as compared with that of the starting apatite material.

EXAMPLE 12

A first solution was made by dissolving 1% by weight of sodium fluoride in a $10^{-1}$ M aqueous solution of orthophosphoric acid having a pH of about 3.

A second solution was made by mixing equal volumes of a $10^{-1}$ M aqueous calcium nitrate solution, $10^{-1}$ M aqueous sodium monohydric orthophosphate solution and $10^{-2}$ M aqueous sodium dihydric orthophosphate solution with the pH adjusted to about 5. After standing, the supernatant liquid was separated from the solid synthetic Brushite residue and its pH was adjusted to 7 by addition of sodium hydroxide.

The first solution is applied topically to teeth and left for about 5 minutes. The second liquid is then subsequently applied topically to the teeth and left for about 5 minutes.

Loss of calcium and orthophosphate from teeth subjected to this procedure is minimised and the deposition of fluoroapatite on the treated surfaces is encouraged. Remineralisation of early carious lesions is promoted and apatitic material deposited in pits and fissures of the enamel.

Each of the solution can be applied from separate containers in a single kit.

Sodium monofluorophosphate can replace sodium fluoride. However, it should be kept separate from orthophosphoric acid solution until the time of use when it can be premixed therewith immediately before use or applied to the teeth in quick succession with the orthophosphoric acid solution. Alternatively, either sodium fluoride or sodium monofluorophosphate may be present in the second solution.

EXAMPLE 13

Preparation of DCPD Substituted by Zinc Ions.

PROCEDURE A

An aqueous slurry of 43 grams of calcium oxide and 4 grams of zinc oxide are added slowly to 170 grams of an 88% aqueous solution of orthophosphoric acid at room temperature. The temperature should not be allowed to rise above 20° C nor the pH to rise above 5.

The rection product formed is DCPD wherein approximately 5 cation % of the calcium ions are replaced by zinc ions.

PROCEDURE B

Procedure A is repeated except that 95 grams of calcium carbonate and 7 grams of zinc carbonate are used in lieu of the calcium oxide and zinc oxide. The same reaction product is formed.

PROCEDURE C

Two liters of an aqueous solution of 105 grams of calcium chloride and 7 grams of zinc chloride, and two liters of an aqueous solution containing 142 grams of dibasic sodium orthophosphate and 10 grams of monobasic sodium orthophosphate are added slowly with stirring to one litre of an aqueous solution containing 20 grams of monobasic sodium orthophosphate at room temperature. The pH must not rise above 5. The product is filtered, washed and dried as described above.

The product is DCPD with approximately 5 cation % of the calcium replaced by zinc.

PROCEDURE D

Procedure C is repeated except that 224 grams of calcium nitrate tetrahydrate and 15 grams of zinc nitrate hexahydrate are used in lieu of calcium chloride and zinc chloride. The reaction product formed is the same as in Procedure C.

Water of crystallisation can be removed from the reaction products of procedures A, B, C and D, by heating to about 200° C, to form ADCP containing zinc ions in place of a portion of the calcium ions.

EXAMPLE 14

The reaction products of the procedures of Example 13 are calcined at 500° C until constant weight is obtained. The calcined product is calcium pyrophosphate in which the percentage of calcium ions replaced by zinc ions is substantially the same as in the uncalcined material.

EXAMPLE 15

The following toothpaste and toothpowder containing a water soluble fluoride and an insoluble fluoride are prepared:

| Ingredients | PARTS Toothpaste | Toothpowder |
|---|---|---|
| FHA* | 40 | — |
| FA* | — | 10 |
| HA* | — | 80 |
| Glycerine | 25 | — |
| Sodium N-lauroyl sarcosinate | 1.0 | — |
| Sodium carboxymethyl cellulose | 1.0 | — |
| Sodium monofluorophosphate | 0.35 | — |
| Sodium fluoride | — | 0.2 |
| Flavours, preservatives, colours etc. | Q.S. to 100 | Q.S. to 100 |

*FHA, FA & HA are each prepared by the procedure set fourth in Example 7 and have monofluorophosphate ions therein. In the case of FHA, the material is first formed in accordance with the procedure of Example 5 such that 25% of the hydroxyl content of HA is replaced by fluoride.

The above toothpaste and toothpowder provide fluoride from the water-soluble fluoride-providing component to protect dental enamel and also include the insoluble apatite material containing monofluophosphate ions which provide apatite material and fluoride to the pits and fissures of dental enamel. Similar provision occurs if FA or FHA, which do not contain monofluorophosphate ions, are employed.

EXAMPLE 16

The following toothpastes are prepared including analytically pure FA prepared in accordance with the procedure of Example 1:

| Ingredients | Parts | |
|---|---|---|
| FA | 10 | 10 |
| ADCP | 30 | — |
| DCPD | — | 30 |
| Glycerine | 25 | 25 |
| Sodium N-lauroyl sarcosinate | 1.0 | 1.0 |
| Sodium carboxymethylcellulose | 1.0 | 1.0 |
| Sodium fluoride | 0.2 | — |
| Sodium monofluorophosphate | — | 0.35 |
| Water, flavouring materials, preservatives, colours, etc. | Q.S. to 100 | Q.S. to 100 |

EXAMPLE 17

The following toothpastes and toothpowders are prepared except that the FA is prepared in accordance with Example 2 and has the crystal morphology of the Brushite precursor.

| Ingredients | Parts Toothpastes | | | | |
|---|---|---|---|---|---|
| | A | B | C | D | E |
| FA | 10 | 10 | 10 | 10 | 10 |
| HA | — | 30 | 15 | — | — |
| ADCP | 30 | — | 15 | — | — |
| DCPD | — | — | — | 30 | — |
| Calcium pyrophosphate | — | — | — | — | 30 |
| Glycerine | 25 | 25 | 25 | 25 | 25 |
| Sodium N-lauroyl sarcosinate | 1.0 | 1.0 | 1.0 | 1.0 | — |
| Sodium lauryl sulphate | — | — | — | — | 1.0 |
| Sodium carboxymethyl cellulose | 1.0 | 1.0 | 1.0 | 1.0 | 1.0 |
| Sodium fluoride | 0.2 | 0.2 | 0.2 | — | — |
| Sodium monofluorophosphate | — | — | — | 0.35 | — |
| Water, flavouring materials, preservatives, colours, etc. | Q.S. to 100 | Q.S. to 100 | Q.S. to 100 | Q.S. to 100 | Q.S. to 100 |

| Ingredients | Parts Toothpowder |
|---|---|
| FA | 10 |
| HA | 80 |
| Sodium fluoride | 0.2 |
| Sodium N-lauroyl sarcosinate | 2.0 |
| Flavour, preservatives, colour, etc. | Q.S. to 100 |

ADCP in toothpastes A and C is prepared as in Example 2 by employing excess DCPD reactant. It has the crystal morphology of its Brushite Precursor.

Calcium pyrophosphate in toothpaste E is prepared as in Example 2 by employing excess DCPD reactant and then calcining the resulting ADCP.

EXAMPLE 18

The toothpastes and toothpowder of Example 17 are again prepared except that the FA employed is prepared as in Example 3. Similarly the ADCP in toothpastes A and C and the calcium pyrophosphate in toothpaste E are obtained in accordance with techniques described in Example 3.

EXAMPLE 19

Toothpastes A and D of Example 17 are prepared except that the FA employed is obtained in accordance with the pH fluctuation technique of Example 4.

EXAMPLE 20

The following toothpastes and toothpowder are prepared. The FHA employed is made in accordance with the pH fluctuation technique of Example 5.

| Ingredients | Parts | | |
|---|---|---|---|
| | Toothpaste A | Toothpaste B | Toothpowder |
| FHA* | 40 | — | — |
| FHA** | — | 20 | 30 |
| ADCP | — | 10 | — |
| DCPD | — | 10 | 60 |
| Glycerine | 25 | 25 | — |
| Sodium N-lauroyl sarcosinate | 1.0 | 1.0 | 2.0 |
| Sodium carboxymethyl cellulose | 1.0 | 1.0 | — |
| Sodium monofluorophosphate | 0.35 | 0.35 | 0.35 |
| Water, flavouring materials, preservatives, colours, etc. | Q.S. to 100 | Q.S. to 100 | — |
| Flavouring materials preservatives, colours, etc. | — | — | Q.S. to 100 |

FHA* is a fluorohydroxyapatite in which fluoride replaces 25% of the hydroxyl content. FHA* is a fluorohydroxyapatite in which fluoride replaces 50% of the hydroxyl content.

EXAMPLE 21

The toothpastes and toothpowder of Example 17 are again prepared except that the FA is made from calcium fluoride and DCPD in accordance with the procedure of Example 6.

EXAMPLE 22

The following toothpastes and toothpowder containing apatite materials containing monofluorophosphate ions prepared in accordance with Example 7 are formulated.

| Ingredients | Parts Toothpastes | | | | |
|---|---|---|---|---|---|
| | A | B | C | D | E |
| FA (with MFP ions) | 10 | 10 | 10 | 10 | — |
| HA (with MFP ions) | — | 30 | 15 | — | — |
| ADCP | 30 | — | 15 | — | 10 |
| DCPD | — | — | — | 30 | 10 |
| FHA (with MFP ions & With 50% of hydroxyl content replaced by fluoride | — | — | — | — | 20 |
| Glycerine | 25 | 25 | 25 | 25 | 25 |
| Sodium N-lauroyl sarcosinate | 1.0 | 1.0 | 1.0 | 1.0 | 1.0' |
| Sodium carboxymethyl cellulose | 1.0 | 1.0 | 1.0 | 1.0 | 1.0 |
| Sodium fluoride | 0.2 | 0.2 | 0.2 | — | — |
| Sodium monofluorophosphate | — | — | — | 0.35 | 0.35 |
| Water, flavouring materials, preservatives, colours, etc. | Q.S. to 100 | Q.S. to 100 | Q.S. to 100 | Q.S. to 100 | Q.S. to 100 |

| Ingredients | Parts Toothpowder |
|---|---|
| FHA (with MFP ions & with 50% of hydroxyl content replaced by fluoride) | 30 |
| DCPD | 60 |
| Sodium monofluorophosphate | 0.35 |
| Flavour, preservatives, colours, etc. | Q.S. to 100 |

EXAMPLE 23

The following toothpastes are prepared using HA having carbonate ions substituted therein, prepared in accordance with the procedure set forth in Example 8.

| Ingredients | Parts | |
|---|---|---|
| | A | B |
| HA (with carbonate atoms) | 50 | 50 |
| Glycerine | 10 | 6 |

-continued

| Ingredients | Parts A | B |
|---|---|---|
| Sorbitol (70%) | 12 | 16 |
| Sodium N-lauroyl sarcosinate | — | 1.0 |
| Sodium lauryl sulphate | 1.0 | — |
| Sodium carboxymethyl cellulose | 1.0 | — |
| Irish moss | — | 1.0 |
| Sodium monofluorophosphate | 0.76 | — |
| Water, flavouring materials, preservatives, colouring etc. | Q.S. to 100 | Q.S. to 100 |

EXAMPLE 24

The following toothpastes and toothpowder are prepared in accordance with the procedure set forth in Example 9. In each of the apatite materials employed, 5 cation % of the calcium ions are replaced by zinc ions.

| Ingredients | PARTS Toothpastes A | B | Toothpowder |
|---|---|---|---|
| FA (with zinc ions) | 10 | — | 10 |
| HA (with zinc ions) | — | — | 80 |
| FHA (with zinc ions & 25% of the hydroxyl content replaced by fluoride) | — | 40 | — |
| Glycerine | 25 | 25 | — |
| Sodium N-lauroyl sarcosinate | 1.0 | 1.0 | 2.0 |
| Sodium carboxymethyl cellulose | 1.0 | 1.0 | — |
| Sodium fluoride | 0.2 | — | 0.2 |
| Sodium monofluorophosphate | — | 0.35 | — |
| Water, flavouring materials preservatives, colouring, etc. | Q.S. to 100 | Q.S. to 100 | — |
| Flavours, preservatives colouring, etc. | — | — | Q.S. to 100 |

EXAMPLE 25

The following toothpaste is prepared employing HA substituted by fluorozincate ions, prepared in accordance with the technique set forth in Example 10:

| Ingredients | Parts |
|---|---|
| Fluorozincate apatite | 5 |
| DCPD | 35 |
| Glycerine | 25 |
| Sodium N-lauroyl sarcosinate | 1 |
| Sodium carboxymethyl cellulose | 1 |
| Water, flavouring materials, preservatives, colours, etc. | Q.S. to 100 |

EXAMPLE 26

DCPD in which zinc ions replace a portion of the calcium ions, prepared in accordance with each of procedures A, B, C and D of Example 13 are employed in the toothpastes and toothpowder below.

In the apatite materials employed, a portion of the calcium ions are also replaced by zinc ions, such apatites are prepared in accordance with the procedure set forth in Example 9.

| Ingredients | PARTS Toothpastes A | B | C | D |
|---|---|---|---|---|
| FA (with zinc ions) | 10 | 10 | 10 | — |
| HA (with zinc ions) | — | 15 | — | — |
| ADCP (with zinc ions) | 30 | 15 | — | 10 |
| DCPD (with zinc ions) | — | — | 30 | 10 |
| FHA (with zinc ions & with 50% of the hydroxyl content replaced by fluoride) | — | — | — | 20 |
| Glycerine | 25 | 25 | 25 | 25 |
| Sodium N-lauroyl sarcosinate | 1.0 | 1.0 | 1.0 | 1.0 |
| Sodium carboxymethyl cellulose | 1.0 | 1.0 | 1.0 | 1.0 |
| Sodium fluoride | 0.2 | 0.2 | — | — |
| Sodium monofluorophosphate | — | — | 0.35 | 0.35 |
| Water, flavouring materials, preservatives, colours, etc. | Q.S. to 100 | Q.S. to 100 | Q.S. to 100 | Q.S. to 100 |

| Ingredients | PARTS Toothpowder |
|---|---|
| DCPD (with zinc ions) | 60 |
| FHA (with zinc ions & 25% of the hydroxyl content replaced by fluoride) | 30 |
| Sodium monofluorophosphate | 0.35 |
| Sodium N-lauroyl sarcosinate | 2.0 |
| Flavouring, preservatives, colours, etc. | Q.S. to 100 |

EXAMPLE 27

The following toothpaste is prepared employing calcium pyrophosphate containing zinc ions in place of a portion of the calcium ions, which is prepared in accordance with that procedure set forth in Example 14:

| Ingredients | Parts |
|---|---|
| Calcium pyrophosphate (with zinc ions) | 45 |
| Glycerine | 10 |
| Sorbitol (70%) | 12 |
| Irish moss | 1.5 |
| Sodium benzoate | 0.5 |
| Sodium saccharine | 0.2 |
| Sodium lauryl sulphate | 1.5 |
| Water, Flavouring oils, colours, etc. | Q.S. to 100 |

EXAMPLE 28 the following mouthwashes containing calcium and phosphate materials in accordance with this invention are prepared:

| Ingredients | Parts A | B |
|---|---|---|
| FA of Example 4 | 4.20 | — |
| FA of Example 7 (with MFP ions) | — | 8.80 |
| Water | 75.00 | 75.00 |
| Ethyl alcohol | 20.20 | 14.86 |
| Sodium monofluorophosphate | — | 0.6 |
| Sodium lauryl sulphate | 0.58 | 0.72 |
| Flavour and colour | 0.02 | 0.02 |

EXAMPLE 29

The following topical gels containing calcium and phosphate materials in accordance with this invention are prepared:

| Ingredients | Parts A | B |
|---|---|---|
| HA of Example 9 (with zinc ions) | 20.00 | — |
| FA of Example 2 | — | 30.00 |

-continued

| Ingredients | Parts A | Parts B |
|---|---|---|
| Glycerine | 8.90 | 9.10 |
| Sorbitol (70% aqueous solution) | 60.00 | 52.50 |
| Ethyl alcohol (95%) | 8.00 | 5.60 |
| Sodium carboxymethyl cellulose | 1.56 | 1.40 |
| Flavour oil | 1.38 | 1.25 |
| Colour | 0.16 | 0.15 |

The above description and examples are intended to be illustrative. Any modification or variation therefrom which conforms to the spirit of the invention is intended to be included within the scope of the claims.

The embodiments of the invention in which an exclusive property of privilege is claimed are defined as follows:

1. A dental cream preparation for remineralising teeth and providing fluoride to pits and fissures of teeth which comprises about 20-75% by weight of liquid selected from the group consisting of water, humectant and mixture thereof and about 0.5-5% by weight of gelling agent proportioned to form an extrudible creamy mass and about 20% by weight to about 99% by weight of a dental polishing or abrasive agent, said polishing or abrasive agent including, in amount of about 10% by weight to about 90% by weight based on the weight of said dental preparation, a material selected from the group consisting of:
   1. fluorapatite;
   2. fluorohydroxyapatite;
   3. apatite, calcium deficient apatite, hydroxyapatite, fluorohydroxyapatite or fluorapatite each containing monofluorophosphate ions;
   4. fluorapatite or fluorohydroxyapatite wherein about 0.1-1% by weight of the calcium content of each is replaced by a non-toxic divalent metal ion selected from the group consisting of zinc, copper, cadmium, nickel, cobalt, iron, manganese, chromium, magnesium strontium and barium; and
   5. hydroxyapatite substituted by a fluoro anion of a non-toxic divalent transition metal;

wherein said material is prepared by a process comprising reacting reactants at ambient temperature initially at about pH 7, maintaining this pH until equilibrium is substantially established, reducing said pH to about 4, maintaining this pH until equilibrium is substantially established, raising the pH to about 7 until equilibrium is reached and crystallite growth occurs, and repeating said fluctuating pH cycle for a total of about 2 to about 5 times terminating at pH 7, wherein said reactants to prepare said materials are selected from the group consisting of:

a. equimolar amounts of hydrofluoric acid in aqueous solution and hydroxyapatite suspended in said solution to form said fluorapatite (1);

b. hydrofluoric acid in aqueous solution and hydroxyapatite suspended in said solution, said hydrofluoric acid being present and being in an amount less than equimolar of the amount of said hydroxyapatite, to form said fluorohydroxyapatite (2);

c. calcium fluoride in aqueous solution and calcium and phosphate reactant selected from the group consisting of $CaHPO_4$; $Ca_5OH(PO_4)_3$; $CaHPO_4 \cdot 2H_2O$; and phosphoric acid and a calcium salt which provides calcium and phosphate reactant to calcium fluoride up to a molar ratio of about 20:1, to form said fluorapatite (1) or said fluorohydroxyapatite (2);

d. a monofluorophosphate salt in aqueous solution and a material selected from the group consisting of apatite, calcium deficient apatite of the formula: $Ca_{10-y}H_y(OH)_{2-y}(PO_4)_6 \cdot nH_2O$ where $0 \leq n \geq 10$ and $0 \leq y \geq 2$, hydroxyapatite, flurohydroxyapatite and fluorapatite, the amount of said monofluorophosphate salt being up to about equimolar to the amount of said material, to form said material (3) which is substituted with monofluorophosphate ions;

e. a water-soluble non-fluoride compound which provides a non-toxic divalent metal ion selected from the group consisting of zinc, copper, cadmium, nickel, cobalt, iron, manganese, chromium, magnesium, strontium and barium and a suspension of fluorapatite or fluorohydroxyapatite to form the fluorapatite or fluorohydroxyapatite (4) material in which about 0.1-1% by weight of the calcium thereof is replaced by said nontoxic divalent metal ion;

f. hydrogen fluoride or a water-soluble alkali metal salt thereof and a suspension of hydroxyapatite to form said fluorapatite or fluorohydroxyapatite (4) in which about 0.1-1% by weight of the calcium thereof is replaced by a non-toxic divalent metal ion selected from the group consisting of zinc, copper, cadmium, nickel, cobalt, iron, manganese, chromium, magnesium, strontium and barium which is formed in a reaction of said process (e) between a water-soluble non-fluoride compound of a compound which provides said non-toxic divalent metal ion and hydroxyapatite in suspension; and g. a compound which provides a fluoride ion and a compound which provides a non-toxic divalent transition metal ion selected from the group consisting of zinc, copper, cadmium, nickel, cobalt, iron, manganese and chromium simultaneously and hydroxyapatite in a slurry, the amount of said divalent transition metal ion being about 0.1-1% by weight of the calcium in said apatite, said compound which provides a fluoride ion being in amount sufficient to react with said transition metal ion, to form said apatite (5) in which orthophosphate groups in said hydroxyapatite are replaced by said fluroanion of the transition metal.

2. The dental preparation of claim 1 wherein said material is formed in accordance with (a) thereof.

3. The dental preparation claimed in claim 1 wherein said material is formed in accordance with (b) thereof.

4. The dental preparation claimed in claim 1 wherein said material is formed in accordance with (c) thereof.

5. The dental preparation claimed in claim 1 wherein said material is formed in accodance with (d) thereof.

6. The dental preparation claimed in claim 1 wherein said material is formed in accordance with (e) thereof.

7. The dental preparation claimed in claim 1 wherein said material is formed in accordance with (f) thereof.

8. The dental preparation claimed in claim 1 wherein said material is formed in accordance with (g) thereof.

9. The dental preparation claimed in claim 1 wherein there is present a water-soluble salt which ionises to produce fluoride ion in amount of about 0.01-1% by weight of fluoride ion in said dental preparation.

10. The dental preparation claimed in claim 9 wherein said salt which ionises to produce fluoride ion is sodium monofluorophosphate.

11. A dental cream preparation for remineralising teeth and providing fluoride to pits and fissures of teeth which comprises about 20–75% by weight of liquid selected from the group consisting of water, humectant and mixture thereof, about 0.5–5% by weight of gelling agent proportioned to form an extrudible creamy mass and about 20% by weight to about 99% by weight of a dental polishing or abrasive agent, said agent including, in amount of about 10% by weight to about 90% by weight, a material selected from the group consisting of fluorapatite and fluorohydroxyapatite in which a portion of calcium is replaced by zinc which material is prepared by reacting said material with an aqueous solution of zinc nitrate which is present in said solution in amount of up to $10^{-2}$M, adjusting the pH of the solution to about 7 and then lowering the pH of the solution to about 4 and then raising it to a pH of about 7 about 3–5 times, providing sufficient time at each of pH 4 and pH 7 levels for equilibrium to be reached and terminating at pH 7, wherein the amount of calcium replaced by zinc corresponds to the amount of zinc in said solution of zinc nitrate.

12. A dental cream preparation for remineralising teeth and providing fluoride to pits and fissures of teeth which comprises about 20–75% by weight of liquid selected from the group consisting of water, humectant and mixture thereof, about 0.5–5% by weight of gelling agent proportioned to form an extrudible creamy mass and about 20% by weight to about 99% by weight of a dental polishing or abrasive agent, said agent including about 5% by weight of an apatite in which about 5% by weight of the phosphate ions are replaced by $ZnF_4^{-2}$ ions which is prepared by reacting apatite simultaneously with $10^{-2}$M sodium fluoride and $10^{-3}$M zinc nitrate aqueous solution, adjusting the pH of the solution to about 7 and then lowering the pH of the solution to about 4 and then raising it to a pH of about 7 about 3–5 times, providing sufficient time at each of pH 4 and pH 7 levels for equilibrium to be reached and terminating at pH 7.

13. A process for preparing materials containing calcium and phosphate selected from the group consisting of:
  1. fluorapatite;
  2. fluorohydroxyapatite;
  3. apatite, calcium deficient apatite, hydroxyapatite, fluorohydroxyapatite or fluorapatite each containing monofluorophosphate ions;
  4. hydroxyapatite containing carbonate ions;
  5. hydroxyapatite, fluorapatite or fluorohydroxyapatite wherein about 0.1–1% by weight of the calcium content of each is replaced by a non-toxic divalent metal ion selected from the group consisting of zinc, copper, cadmium, nickel, cobalt, iron, manganese, chromium, magnesium strontium and barium; and
  6. hydroxyapatite substituted by a fluoranion of a non-toxic divalent transistion metal;

comprising reacting reactants at ambient temperature initially at about pH 7, reducing said pH to about 4, maintaining this pH until equilibrium is substantially established, raising the pH to about 7 until equilibrium is reached and crystallite growth occurs, and repeating said fluctuating pH cycle for a total of about 2 to about 5 times terminating at pH 7, wherein said reactants to prepare said materials are selected from the group consisting of:

a. equimolar amounts of hydrofluoric acid in aqueous solution and hydroxyapatite suspended in said solution to form fluoroapatite 1;

b. hydrofluoric acid in aqueous solution and hydroxyapatite suspended in said solution said hydrofluoric acid being present and being in an amount less than equimolar of the amount of said hydroxyapatite, to form said fluorohydroxyapatite 2;

c. calcium fluoride in aqueous solution and calcium and phosphate reactant selected from the group consisting of $CaHPO_4$; $Ca_5OH(PO_4)_3$; $CaHPO_4.2H_2O$; and phosphoric acid and a calcium salt which provides calcium ions in a molar excess of calcium and phosphate reactant to calcium fluoride up to a molar ratio of about 20:1, to form said fluorapatite 1 or said fluorohydroxyapatite 2;

d. a monofluorophosphate salt in aqueous solution and a material selected from the group consisting of apatite, calcium deficient apatite of the formula: $Ca_{10-y}H_y(OH)_{2-y}(PO_4)_6 \cdot nH_2O$ where $0 \geq n \leq 10$ and $0 \geq y \leq 2$, hydroxyapatite, fluorohydroxyapatite and fluorapatite, the amount of said monofluorophosphate salt being up to about equimolar to the amount of said material, to form said material 3 which is substituted with monofluorophosphate ions;

e. an alkali metal carbonate or bicarbonate and hydroxyapatite in aqueous solution, the amount of said carbonate or bicarbonate being such as to return the pH to 7 from pH 4, to form said hydroxyapatite containing carbonate ions 4 which carbonate ions are incorporated in the crystal lattice of said hydroxyapatite; which hydroxyapatite containing carbonate ions has surface properties similar to those of talc;

f. a water-soluble non-fluoride compound which provides a non-toxic divalent metal ion selected from the group consisting of zinc, copper, cadmium, nickel, cobalt, iron, manganese, chromium, magnesium, strontium and barium and a suspension of hydroxyapatite, fluorapatite and fluorohydroxyapatite to form the hydroxyapatite, fluorapatite or fluorohydroxyapatite 5 material in which about 0.1–1% by weight of the calcium thereof is replaced by said non-toxic divalent metal ion;

g. hydrogen fluoride or a water-soluble alkali metal salt thereof and a suspension of hydroxyapatite formed in accordance with (f) above to form said fluorapatite or fluorohydroxyapatite 5 in which about 0.1–1% by weight of the calcium thereof is replaced by said non-toxic divalent metal ion recited in (f) above; and h. a compound which provides a fluoride ion and a compound which provides a non-toxic divalent transition metal ion selected from the group consisting of zinc, copper, cadmium, nickel, cobalt, iron, manganese and chromium simultaneously and hydroxyapatite in a slurry, the amount of said divalent transition metal ion being about 0.1–1% by weight of the calcium in said apatite, said compound which provides a fluoride ion being in amount sufficient to react with said transition metal ion, to form said apatite 6 in which orthophosphate groups in said hydroxyapatite are replaced by said fluoranion of the transition metal.

14. The process of claim 13 wherein a base selected from the group consisting of ammonia, ammonium hydroxide and triethanolamine is employed to adjust the pH at about 7 and an acid selected from the group consisting of nitric acid and hydrogen chloride is employed to adjust the pH at about 4.

15. The process of claim 14 wherein the pH is fluctuated from about 7 to about 4 to about 7 about three times.

16. The process of claim 14 wherein said reactants (a) are employed.

17. The process of claim 14 wherein said reactants (b) are employed.

18. The process of claim 14 wherein said reactants (c) are employed.

19. The process of claim 14 wherein said reactants (d) are employed.

20. The process of claim 14 wherein said monofluorophosphate salt is sodium monofluorophosphate.

21. The process of claim 14 wherein said reactants (e) are employed.

22. The process of claim 21 wherein said alkali metal carbonate or bicarbonate is sodium carbonate or bicarbonate.

23. The process of claim 14 wherein said reactants (f) are employed.

24. The process of claim 23 wherein said divalent metal ion is zinc.

25. The process of claim 14 wherein said reactants (g) are employed.

26. The process of claim 25 wherein said divalent metal ion is zinc.

27. The process of claim 14 wherein said reactants (h) are employed.

28. The process of claim 27 wherein said divalent transition metal is zinc.

29. A process of introducing zinc into hydroxyapatite comprising contacting hydroxyapatite material with an aqueous solution of zinc nitrate wherein said zinc nitrate is present in said solution in amount of up to $10^{-2}$M, adjusting the pH of the solution to about 7 and then lowering the pH of the solution to about 4 and then raising it to a pH of about 7 about 3–5 times, providing sufficient time at each of pH 4 and pH 7 levels for equilibrium to be reached and terminating at pH 7.

30. A process of introducing copper ions into hydroxyapatite comprising contacting hydroxyapatite material with a $10^{-2}$M cupric nitrate solution, adjusting the pH of the solution to about 7 and then lowering the pH of the solution to about 4 and then raising it to a pH of about 7 about 3–5 times, providing sufficient time at each of pH 4 and pH 7 levels for equilibrium to be reached and terminating at pH 7.

31. A process of introducing chromium ions into hydroxyapatite comprising contacting hydroxyapatite material with a $10^{-2}$M chromous chloride solution, adjusting the pH of the solution to about 7 and then lowering the pH of the solution to about 4 and then raising it to a pH of about 7 about 3–5 times, providing sufficient time at each of pH 4 and pH 7 levels for equilibrium to be reached and terminating at pH 7.

* * * * *